United States Patent [19]

Hayashi

[11] Patent Number: 4,994,240
[45] Date of Patent: Feb. 19, 1991

[54] SUCTION HEAD AND CARRYING REACTION CUPS USED IN BIOCHEMICAL REACTION ANALYZING APPARATUS

[75] Inventor: Hidechika Hayashi, Yokohama, Japan

[73] Assignee: Tosoh Corporation, Shinnanyo, Japan

[21] Appl. No.: 506,536

[22] Filed: Apr. 6, 1990

Related U.S. Application Data

[63] Continuation of Ser. No. 146,827, Jan. 11, 1988, abandoned.

[30] Foreign Application Priority Data

Jun. 10, 1986 [JP] Japan ................ 61-134446

[51] Int. Cl.$^5$ .............................................. G01N 35/00
[52] U.S. Cl. ...................................... 422/63; 422/102; 294/64.1
[58] Field of Search ............... 422/63, 64, 65, 100, 422/102; 271/97; 294/64.1; 414/737

[56] References Cited

U.S. PATENT DOCUMENTS 3,841,687 10/1974 Banyas et al. ................ 294/64 R
4,650,233 3/1987 Mang et al. .................... 294/64.1
4,662,668 5/1987 Hufford ......................... 294/64.1
4,801,429 1/1989 Torfs et al. ..................... 422/63

FOREIGN PATENT DOCUMENTS 3325207 1/1985 Fed. Rep. of Germany ..... 294/64.1
48-20790 6/1973 Japan .
49-52978 5/1974 Japan .
60-45691 3/1985 Japan .
61-20287 2/1986 Japan .
61-99434 6/1986 Japan .

Primary Examiner—Robert J. Warden
Assistant Examiner—D. John Griffith, Jr.
Attorney, Agent, or Firm—Oblon, Spivak, McClelland, Maier & Neustadt

[57] ABSTRACT

A biochemical reaction analyzing apparatus having a reaction cup and a suction head for carrying the reaction cup, wherein the suction head can carry a reaction cup of light weight used for biochemical reaction analysis by hanging it by suction, wherein the head is provided with a cylindrical cavity as an air passage having a diameter approximately equal to that of an air suction and discharge opening formed at the lower end of the head body and extending up from the opening in the head body; further, if necessary, a plurality of circumferential grooves formed in the inner wall surrounding the cylindrical cavity or a vertically movable weight fitted in the cylindrical cavity is provided.

4 Claims, 2 Drawing Sheets

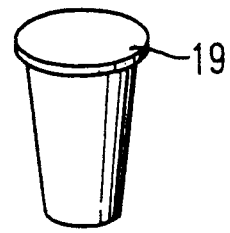
FIG. 3
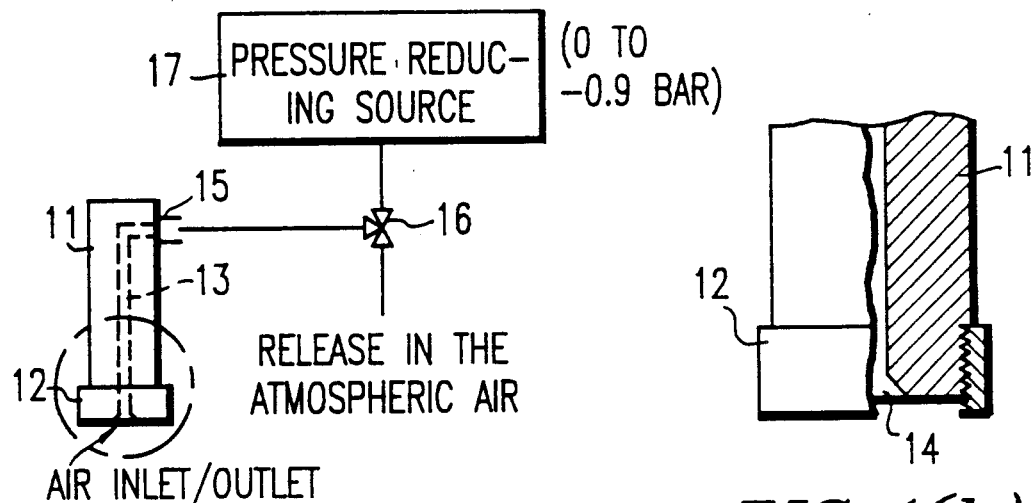
FIG. 4(a)
PRIOR ART
FIG. 4(b)
PRIOR ART
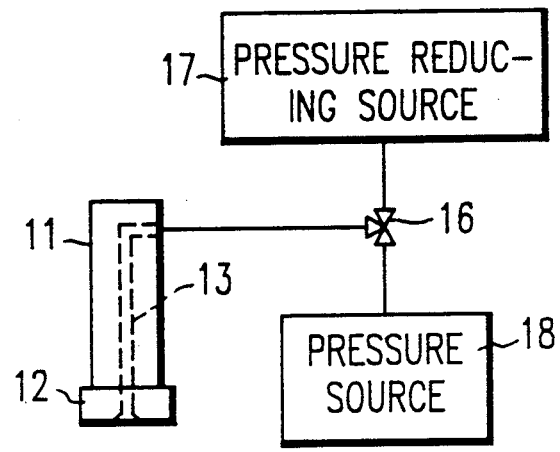
FIG. 5
PRIOR ART

SUCTION HEAD AND CARRYING REACTION CUPS USED IN BIOCHEMICAL REACTION ANALYZING APPARATUS

This application is a continuation of application Ser. No. 146,827, filed Jan. 11, 1988, now abandoned.

DESCRIPTION

1. Technical Field:

The present invention relates to a suction head for carrying reaction cups to be used suitably in, for example, an analyzing apparatus for detection and measurement of a very small amount of biologically active substances contained in a specimen solution, particularly EIA (Enzyme Immuno Assay) apparatus.

2. Background Art:

The present invention will be described below by referring to its typical application, Enzyme Immuno Assay method, wherein enzyme is used as a label for an antigen-antibody reaction complex. Recently, active efforts have been made in the research and development of the EIA method, as one of immunological techniques for detecting and measuring very small amounts of biologically active substances.

There are many types of EIA methods. A method is known typically wherein an amount of antibody or antigen in a specimen solution is quantitatively analyzed by contacting the solution with an antigen or antibody fixed on an an insoluble carrier and a conjugate labeled with enzyme so as to produce a complex through the reaction of immune reaction, contacting the produced complex with a substrate which can produce an optically detectable variation in its characteristics (for example, fluorescent intensity) under the activating action of the enzyme, and determining the optical variation of the substrate.

Since these analytical operations were generally performed on many specimens, analyzing apparatuses comprising a number of reaction cells such as the known multi-titre plate has been conventionally provided for practical use.

However, these operations using multi-titre plate present inconveniences in that they require time-consuming preparation for the analyzing process if assays of different analytes are applied to individual samples, though they are effectively appropriate to assay of the same analyte or the same group of analytes for each specimen.

In these circumstances, the inventors have completed such a system as described below to improve the operability and the efficiency of operation in the practical applications of the EIA method.

This system is used with sealed cups, filled with a specific antibody (or antigen) fixed on an insoluble carrier (for example, bead) and conjugate (this cup will be referred to as "reaction cup" hereinafter). A group of reaction cups is prepared for each analyte. Before the analyzing operations are undertaken, this system can select the reaction cups corresponding to the required analytes for each specimen from among the prepared groups of reaction cups, and carry them on a transport them block and then transport to an analyzing section.

Such a system is characterized by the fact that it can be very effectively used for an automated analyzing apparatus. For example, if the system comprises a cup lifter of the x/y scanning type in a storage containing a group of reaction cups corresponding to each of many analytes, and it can repeat the sequential operations of hanging a specific reaction cup and carrying it onto the transport block by running the cup lifter over the storage, the use of an electronic control unit will allow the cup lifter to arrange the reaction cups for the respective analytes automatically and mechanically on the transport block according to the required data stored in the control unit.

A suction head, for example, as shown in FIG. 4, can be used as a part of the cup lifter for the system as described above. However, the use of this suction head in the system encountered the problems described below.

The suction head as shown in FIGS. 4(a) and 4(b) comprise a head body 11, a suction pad 12 of elastic ring fixed on the lower end of the head body 11, and an air passage 13 provided with an air suction port 14 opened at the central bottom part of the elastic pad 12 and another port 15 connected to a pressure reducing source 17 through a change-over valve 16. This suction head attracts the reaction cup as described above at the lower end of the suction pad 12 by the aid of vacuum, and hangs it by suction. Although there was no problem in the suction hanging of the reaction cup, the suction pad encountered a problem in that the reaction cup 19, being very light, is hardly separated from the suction pad 12 because of its adhesion when it is placed down on the transport block. As shown in FIG. 5, the change-over valve 16 was switchably connected between the pressure reducing source 17 and a pressure source 18, which permits it to discharge air through the suction port 14 for the forced separation of the cup 19 from the suction pad 12. However, this configuration as shown in FIG. 5 sometimes caused a difficulty in the separation of the cup 19 from the suction pad 12.

The present invention was produced to provide a device effectively applicable to the system using reaction cups as described above. Particularly, an objective of the present invention is to provide a suction head which can be used to select and carry the reaction cup, as used in the above-described system, in a storage of many reaction cups, particularly a suction head which can provide the stable operations of lifting up and placing down the reaction cup.

DISCLOSURE OF INVENTION

According to the present invention produced to accomplish this object, the suction head for carrying reaction cups used in a biochemical reaction analyzing apparatus is characterized by the facts that it can engage with the sealed-up top face of a reaction cup, which comprises a hollow body constituting a reaction cell for biochemical reaction as well as a top covered and sealed up with a sheet, and carry the reaction cup by hanging it by suction, and it comprises a suction pad of elastic ring at its lower end to engage with the periphery of the reaction cup top face, a head body provided with an air suction and discharge opening formed inside the suction pad, and a cylindrical cavity approximately equal in diameter to the opening and extending up from the opening in the axial direction of the head body long enough to guide the discharged air stream downward.

In the suction head thus constructed, the head body provided with the cylindrical cavity may be provided with a plurality of circumferential grooves in its inner wall. It is also effective that a weight of light load engageable with the top of the reaction cup freely moves vertically in the cylindrical cavity or passage so as to exert a mechanical downward force on the reaction cup to be placed down in position. It is also effective to exert a downward force on the weight by using a spring of small load.

The present invention utilizes this construction of the suction head for the reason as described below.

The inventors found that in the construction as shown in FIG. 5, if the suction of the reaction cup by the suction pad is caused by the horn type air suction and discharge port of the head body, the discharge air tends to suck the reaction cup up to the suction pad according to the Bernoulli's principle. Based upon this knowledge, the inventors invented the construction of the suction head according to the present invention wherein the effect of suction given by the discharge air on the reaction cup was eliminated.

For the EIA process, the present invention preferably uses a reaction cup which is filled up with a specific antibody (or antigen) fixed on the surfaces of synthetic resin beads as material contributing to the immunological reaction. However, the reaction cup may not be limited to such a cup.

In many cases, the reaction cup is a cup of transparent or opaque synthetic resin having a capacity as small as several milliliters or less and a weight of approximately 10g or less.

The sealing sheet over the top of the reaction cup is a foil that is so fragile so as to be easily broken by a sharp tool or equivalent, or generally a metallic foil such as aluminium or a plastic film coated with aluminium. However, the material of the sealing sheet is not limited to them. The sealing foil must be tightly attached by heat sealing or bonding onto the periphery of the to opening.

BRIEF DESCRIPTION OF DRAWINGS

FIG. 3 is a perspective view illustrating the construction of the reaction cup according to the present invention.

FIG. 4(a) is a frontal view showing a conventional suction head.

FIG. 4(b) is a partial enlarged view with a sectional view in the right half part showing the detail of the suction head as shown in FIG. 4(a).

FIG. 5 is a frontal view showing another conventional suction head.

BEST MODE FOR CARRYING OUT THE INVENTION

Figure 1A:
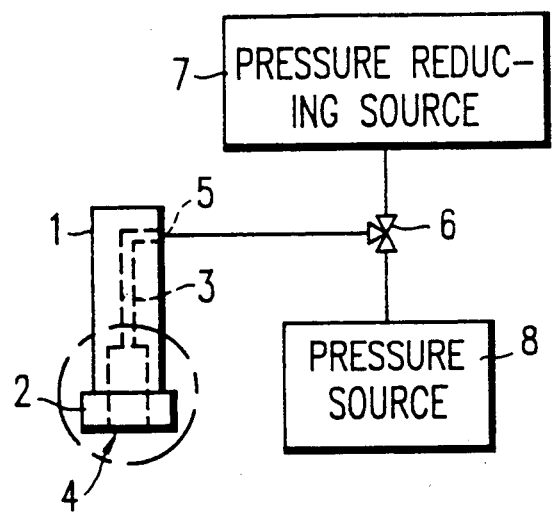
FIG. 1(a) is a front view illustrating the construction of an embodiment of the suction head according to the present invention.

The present invention will be described below by using the embodiments as shown in the drawings annexed hereto.

Figure 1B:
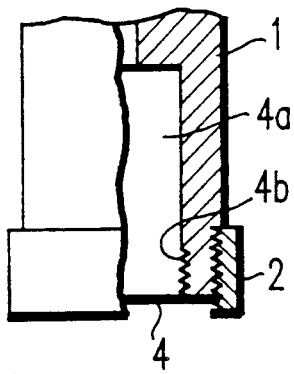
FIG. 1(b) is a partial enlarged view with a sectional view in the right half part showing the detail of the suction head as shown in FIG. 1(a).

In FIGS. 1(a) and 1(b), the head body 1 of the suction head is supported by a movable support (not shown) so that it can be moved in a horizontal plane. This movable support is generally controlled by a proper electronic control unit so that it can be horizontally and vertically moved to scan, lift and lower the reaction cup.

At the lower end of the head body 1, a suction pad of elastic ring 2 is fixedly mounted so that the lower end of the pad 2 can engage with the top of the reaction cup 19.

An air passage 3 is provided with an air suction and discharge port 4 formed as a larger opening at the lower end of the head body 1 (inside the suction pad 2). The other end 5 of the air passage 3 is switchably connected to a pressure reducing source 7 and a pressure source 8 through a change-over valve 6.

This embodiment of the suction head according to the present invention is characterized by the fact that a cylindrical cavity 4a having the same diameter as the air suction and discharge port 4 is formed above the air suction and discharge port 4 (in the axial direction of the head body) at a predetermined length. A plurality of circumferential grooves 4b are formed in the inner wall surrounding the cylindrical cavity 4a.

The cylindrical cavity 4a constituting a part of the air passage 3 is effective to separate the reaction cup 19 forcedly from the suction pad 2 by the aid of the air discharge pressure, when the reaction cup 19 is placed down on a transport block. To eliminate the effect of suction according to the Bernoulli's principle as described above, it is desirable that the area on the top face of the sealing sheet over the reaction cup where the discharged air is blown down is as large as possible, that the area on the top face of the sealing sheet where the air flows in parallel to the top face of the sheet is thus as small as possible, and that the diameter of the former area is set according to the conditions where the reaction cup can be separated from the suction pad. In general, the diameter of the air-blown area is desirably 50% to 90% of the suction pad inner diameter.

It is also desirable that the axial length of the cylindrical cavity 4a is set so as to melt the conditions in which the air discharged through the narrow air passage 3 is blown down on the reaction cup through the entire cross sectional area of the discharge port 4. In general, the axial length of the cylindrical cavity 4a is desirably equal to or greater than ½ the diameter of the discharge port 4.

The air suction force and the air discharge force used for the lifting of the reaction cup by the suction head according to this embodiment is generally approximately −0.9 atm to −0.2 atm and approximately 0.1 atm to 2 atm respectively.

The reaction cup lifting test was conducted by using this embodiment of the suction head according to the present invention in the conditions as described below, and the results were compared with the results of the same test on the suction head as shown in FIG. 5 (substantially identical with the suction head according to this embodiment, except that it has no cylindrical cavity). The comparison showed that the working stability was higher for the embodiment according to the present invention, as indicated in Table 1.

The embodiment according to the present invention

| Reaction cup | |
|---|---|
| Top diameter of aluminium foil seal | 14 mm |
| Bottom diameter of cup | 10 mm |
| Weight | 1 g |
| Suction head | |
| Air passage | |
| Diameter | 2 mm |
| Air suction pressure | −0.5 atm |

-continued

| | |
|---|---|
| Air discharge pressure | 0.5 atm |
| Cylindrical cavity | |
| Diameter | 5 mm |
| Axial length | 20 mm |
| Peripheral grooves | 1 mm (3 grooves) |
| Suction pad (of rubber) | |
| Inner diameter | 8 mm |
| Outer diameter | 14 mm |
| The length of the projection from the lower end of the head body | 0.5 mm |

TABLE 1

| Of 100 reaction cups moved from the storage into a transport block, the number of reaction cups failed in movement | |
|---|---|
| Conventional suction head (FIG. 5) | 1 to 10 or more |
| This embodiment (FIG. 1) | 1 or less |

The present invention is not limited to the embodiment as described above. As it is shown in FIGS. 2(a) to 2(c), a vertically movable weight may be freely moved in the cylindrical cavity 4a in the head body 1 and engaged with the top face of the reaction cup to facilitate the separation of the reaction cup from the suction pad 2. 4c is a stopper flange part which projects at the lower end of the head body in the radial and inward direction of the cylindrical cavity 4a to prevent the weight from slipping off.

Figure 2A:
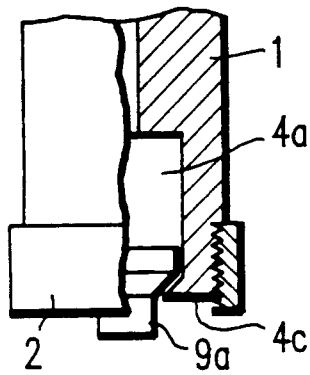
FIGS. 2(a) to 2(c) are partial enlarged views with sectional views in the right half parts showing the other embodiments of the suction head according to the present invention.

FIG. 2(a) shows an embodiment using a pin type weight 9a. FIG. 2(b) shows an embodiment using a ball type weight 9b. FIG. 2(c) shows an embodiment using a pin type weight 9a combined with an energizing spring 10 which exerts a spring force down on the weight 9a. The weight may be of steel, for example, and approximately 0.5 g in weight. The material and weight are not limited. If the energizing spring 10 is used, it is desirable that the spring force is not greater than ½ the suction force exerted by the suction pad 2 on the reaction cup 19. The weight 9a and the stopper flange part 4c are so precisely worked that they can engage with each other so tightly to cause little air leakage.

Figure 2B:
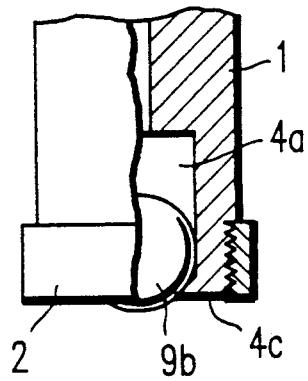
Figure 2C:
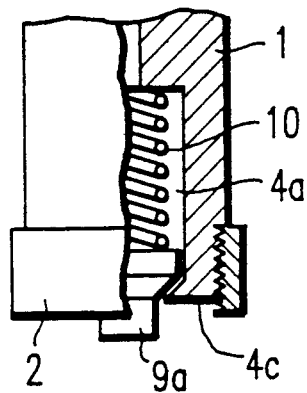

In these embodiments as shown in FIGS. 2(a) to 2(c), the reaction cup 19 can be effectively separated from the suction pad 2 with the energizing spring when it is placed down on a transport block, as in the embodiment as shown in FIG. 1. In addition, these embodiments present the advantages that the forced separation of the reaction cup can assure a larger range of air discharge pressures than that in the embodiment as shown in FIG. 1, because the air discharge may be small enough and the pressed-down weight can prevent the air from flowing further and consequently the reaction cup and other parts near the suction head from being blown away.

The suction head as shown in FIG. 2(c) was tested in the same conditions as the device as shown in FIG. 1, and the results were compared with those of the suction head as shown in FIG. 5. The comparison revealed that the working stability was remarkably higher for the embodiment as shown in FIG. 2(c), as shown in Table 2.

TABLE 2

| Of 100 reaction cups moved from the storage to a transport block, the number when reaction cups failed in movement | |
|---|---|
| Conventional suction head (FIG. 5) | 1 to 10 or more |
| This embodiment (FIG. 2(c)) | 0 |

Industrial Applicability

The suction head according to the present invention presents the advantages that it can be effectively used to carry reaction cups selectively in a storage of many reaction cups in a system using reaction cups, and that it can assure a stable operation of lifting a reaction cup.

I claim:

1. A biochemical reaction analyzing apparatus comprising a reaction cup, a suction head for carrying said reaction cup, means for reducing the pressure in said suction head, and means for increasing the pressure in said suction head; wherein said cup has a hollowed portion providing a reaction cell for biochemical reactions and a top face covered and sealed with a sheet, said suction head being engagable with the sealed top face of the cup, said suction head further comprising: an annular elastic suction pad at its lower end which engages with the top face of the cup to engage with the periphery of the top face of the cup, and a head body provided with an air suction and discharge opening formed inside said suction pad, said head body defining a cylindrical cavity at its lower end and an air passage at its upper end, said cylindrical cavity having a diameter which is substantially equal to a diameter of said opening, said air passage having a diameter which is smaller than the diameters of said cylindrical cavity and said opening, said cylindrical cavity extending up from said opening in a vertical direction and having a length in the vertical direction sufficient to permit a stream of discharged air from said air passage to be guided downward onto the reaction cup through an entire cross-sectional area of said opening;

wherein the length of said cylindrical cavity is equal to or greater than half the diameter of the air suction and discharge opening.

2. An apparatus according to claim 1, wherein a plurality of circumferential grooves are formed on an inner wall of said head body provided with said cylindrical cavity.

3. An apparatus according to claim 1, wherein a weight engageable with said top face of said reaction cup is provided within said cylindrical cavity, said weight being freely movable in the vertical direction in said cylindrical cavity.

4. A suction head according to claim 3, wherein the weight is exerted downwardly by a spring.

* * * * *